United States Patent
Strebelle et al.

(10) Patent No.: US 7,960,595 B2
(45) Date of Patent: *Jun. 14, 2011

(54) PROCESS FOR THE MANUFACTURE OF 1,2-DICHLOROETHANE

(75) Inventors: Michel Strebelle, Brussels (BE); Dominique Balthasart, Brussels (BE)

(73) Assignee: SOLVAY (Société Anonyme), Brussels (BE)

( * ) Notice: Subject to any disclaimer, the term of this patent is extended or adjusted under 35 U.S.C. 154(b) by 137 days.

This patent is subject to a terminal disclaimer.

(21) Appl. No.: 11/722,607

(22) PCT Filed: Dec. 21, 2005

(86) PCT No.: PCT/EP2005/057048
§ 371 (c)(1),
(2), (4) Date: Jun. 22, 2007

(87) PCT Pub. No.: WO2006/067192
PCT Pub. Date: Jun. 29, 2006

(65) Prior Publication Data
US 2008/0207967 A1 Aug. 28, 2008

(30) Foreign Application Priority Data

Dec. 23, 2004 (FR) .................... 04 13873
Apr. 1, 2005 (FR) .................... 05 03252
Apr. 1, 2005 (FR) .................... 05 03258

(51) Int. Cl.
*C07C 17/00* (2006.01)
*C07C 17/15* (2006.01)

(52) U.S. Cl. ........ 570/223; 570/224; 570/225; 570/243; 570/244; 526/62

(58) Field of Classification Search .................. 570/223, 570/224, 244, 225, 243; 526/62
See application file for complete search history.

(56) References Cited

U.S. PATENT DOCUMENTS 2,077,382 A * 4/1937 Engs et al. .................... 570/234
(Continued)

FOREIGN PATENT DOCUMENTS

CN 87101663 9/1988
(Continued)

OTHER PUBLICATIONS

U.S. Appl. No. 12/304,297, filed Dec. 11, 2008, Balthasart, et al.
U.S. Appl. No. 12/304,329, filed Dec. 11, 2008, Strebelle, et al.
U.S. Appl. No. 12/304,379, filed Dec. 11, 2008, Balthasart, et al.
U.S. Appl. No. 12/304,434, filed Dec. 11, 2008, Strebelle, et al.

(Continued)

*Primary Examiner* — Porfirio Nazario Gonzalez
*Assistant Examiner* — Yate K Cutliff
(74) *Attorney, Agent, or Firm* — Oblon, Spivak, McClelland, Maier & Neustadt, L.L.P.

(57) ABSTRACT

Process for the manufacture of 1,2-dichloroethane starting with a hydrocarbon source according to which: a) the hydrocarbon source is subjected to cracking which produces a mixture of products containing ethylene and other constituents; b) the said mixture of products is separated into at least one fraction containing ethylene and into a heavy fraction (fraction C); c) the fraction or fractions containing ethylene are conveyed to a chlorination reactor and/or to an oxychlorination reactor, in which reactors most of the ethylene present is converted to 1,2-dichloroethane; d) the 1,2-dichloroethane obtained is separated from the streams of products derived from the chlorination and oxychlorination reactors and it is conveyed to the pyrolysis oven; and e) the fraction C is conveyed to cracking or to the oven for pyrolysis of 1,2-dichloroethane as fuel.

20 Claims, 1 Drawing Sheet

U.S. PATENT DOCUMENTS

| | | | | |
|---|---|---|---|---|
| 3,864,409 | A | * | 2/1975 | Pope .............................. 570/219 |
| 5,488,190 | A | * | 1/1996 | Le Blevec et al. ............ 570/226 |
| 5,789,499 | A | * | 8/1998 | Masuko et al. ................. 526/62 |
| 6,437,204 | B1 | | 8/2002 | Benje et al. |
| 2007/0142682 | A1 | | 6/2007 | Strebelle et al. |
| 2007/0161830 | A1 | | 7/2007 | Strebelle |

FOREIGN PATENT DOCUMENTS

| | | |
|---|---|---|
| EP | 0 567 381 | 10/1993 |
| WO | WO 97/24306 | 7/1997 |
| WO | 03 048088 | 6/2003 |

OTHER PUBLICATIONS

Zimmermann, H. et al.,"Ethylene", Ullmann's Encyclopedia of Industrial Chemistry-John Wiley & Sons, Inc., pp. 1 of 4-47 of 4, 2000. XP-002356911.

U.S. Appl. No. 11/722,587, filed Jun. 22, 2007, Strebelle, et al.

U.S. Appl. No. 11/722,603, filed Jun. 22, 2007, Strebelle, et al.

U.S. Appl. No. 11/722,589, filed Jun. 22, 2007, Balthasart, et al.

U.S. Appl. No. 11/722,598, filed Jun. 22, 2007, Strebelle, et al.

U.S. Appl. No. 12/919,101, filed Aug. 24, 2010, Petitjean, et al.

* cited by examiner

PROCESS FOR THE MANUFACTURE OF 1,2-DICHLOROETHANE

The present invention relates to a process for the manufacture of 1,2-di-chloroethane (DCE), a process for the manufacture of vinyl chloride (VC) and a process for the manufacture of polyvinyl chloride (PVC).

To date, ethylene which is more than 99.8% pure is normally used for the manufacture of DCE essentially intended for the manufacture of VCM. This ethylene of very high purity is obtained via the cracking of various petroleum products, followed by numerous complex and expensive separation steps in order to isolate the ethylene from the other products of cracking and to obtain a product of very high purity. The other cracking products, in particular ethane and compounds containing at least 3 carbon atoms, are in this case generally isolated and upgraded as a pure product.

Given the high cost linked to the production of ethylene of such high purity, various processes for the manufacture of DCE using ethylene having a purity of less than 99.8% have been developed. These processes have the advantage of reducing the costs by simplifying the course of separating the product resulting from the cracking and by thus abandoning complex separations which are of no benefit for the manufacture of DCE. These processes have, nevertheless, the disadvantage that the ethane and the compounds containing at least 3 carbon atoms, carried with the so-called impure ethylene fraction, which are possibly separated later, are not upgraded, thus putting a strain on the economy of the process.

The aim of the present invention is therefore to provide a process using ethylene with a purity of less than 99.8% which has the advantage of reducing the costs by abandoning complex separations for isolating the ethylene from the other products of cracking which are of no benefit for the manufacture of DCE, but which also have the advantage of allowing upgrading of the ethane and the compounds containing at least 3 carbon atoms, thus bringing about significant savings.

To this effect, the invention relates to a process for the manufacture of DCE starting with a hydrocarbon source according to which:
a) the hydrocarbon source is subjected to cracking which produces a mixture of products containing ethylene and other constituents;
b) the said mixture of products is separated into at least one fraction containing ethylene and into a heavy fraction (fraction C);
c) the fraction or fractions containing ethylene are conveyed to a chlorination reactor and/or to an oxychlorination reactor, in which reactors most of the ethylene present is converted to DCE;
d) the DCE obtained is separated from the streams of products derived from the chlorination and oxychlorination reactors and it is conveyed to the pyrolysis oven; and
e) the fraction C is conveyed to cracking or to the oven for pyrolysis of DCE as fuel.

The hydrocarbon source considered may be any known hydrocarbon source. Preferably, the hydrocarbon source subjected to cracking (step a)) is chosen from the group consisting of naphtha, gas oil, natural gas liquid, ethane, propane, butane, isobutane and mixtures thereof. In a particularly preferred manner, the hydrocarbon source is chosen from the group consisting of ethane, propane and propane/butane mixtures. Good results were obtained with a hydrocarbon source chosen from the group consisting of propane and propane/butane mixtures. The propane/butane mixtures may exist as such or may consist of mixtures of propane and butane.

The expression ethane, propane, butane and propane/butane mixtures is understood to mean, for the purposes of the present invention, products that are commercially available, namely that consist mainly of the pure product (ethane, propane, butane or propane/butane as a mixture) and secondarily of other saturated or unsaturated hydrocarbons, which are lighter or heavier than the pure product itself.

The expression cracking (step a)) is understood to mean, for the purposes of the present invention, all the steps for treating the hydrocarbon source which lead to the formation of a mixture of products containing ethylene and other constituents.

Such a cracking may be carried out according to any known technique as long as it allows the production of a mixture of products containing ethylene and other constituents. Advantageously, the cracking comprises a first step of pyrolysis (that is to say a conversion under the action of heat) of the hydrocarbon source in the presence or absence of third compounds such as water, oxygen, a sulphur derivative and/or a catalyst. This step advantageously takes place in an oven called cracking oven. This first step is preferably followed by steps for thermal recovery of the heat of the cracked gases, for separating the heavy products (for example via organic quenching and aqueous quenching), for compressing and drying the gases and for removing most of the carbon dioxide and most of the sulphur compounds present or added (for example by means of an alkaline washing), optionally for hydrogenating the undesirable derivatives generated during the first pyrolysis step such as for example acetylene and optionally the removal of part of the hydrogen and/or of the methane, for example via a PSA (pressure swing adsorption) process or via a membrane process.

Advantageously, in the process according to the invention, the mixture of products containing ethylene and other constituents derived from step a) comprises hydrogen, methane, compounds comprising from 2 to 7 carbon atoms, carbon monoxide, nitrogen and oxygen. The hydrogen, the methane and the compounds comprising from 2 to 7 carbon atoms other than acetylene are preferably present in an amount of at least 200 ppm by volume relative to the total volume of the said mixture of products. The carbon monoxide, the nitrogen, the oxygen and the acetylene may be present in an amount of less than 200 ppm by volume or in an amount of at least 200 ppm by volume relative to the total volume of the said mixture of products. Compounds containing more than 7 carbon atoms, carbon dioxide, hydrogen sulphide and other sulpho compounds and water may also be present in the abovementioned mixture of products in an amount of less than 200 ppm by volume relative to the total volume of the said mixture of products.

After step a) for cracking defined above, the mixture of products containing ethylene and other constituents is subjected to step b) which advantageously comprises a maximum of four, preferably a maximum of three separation steps in order to obtain the fraction or fractions containing ethylene.

During step b), the mixture of products is separated into at least one fraction containing ethylene and into a heavy fraction (fraction C). Fraction C advantageously contains ethane and compounds comprising at least 3 carbon atoms. Advantageously, these compounds comprising at least 3 carbon atoms result from the mixture of products containing ethylene and other constituents derived from step a) or are generated by side reactions during step b). Among the compounds comprising at least 3 carbon atoms, there may be mentioned propane, propene, butanes and their unsaturated derivatives as well as all the saturated or unsaturated heavier compounds.

According to a first variant of the process according to the invention, fraction C is conveyed to cracking, preferably to the first cracking step which is the pyrolysis step.

According to a first subvariant, the entire fraction C is advantageously conveyed either as raw material or as fuel to cracking.

According to a second subvariant, fraction C is advantageously subjected to a hydrogenation step prior to this step of conveying to cracking.

According to a first embodiment of this second subvariant mentioned above, the hydrogenation step is advantageously followed by conveying the entire fraction C to cracking either as raw material or as fuel.

According to a second embodiment of the second subvariant mentioned above, the hydrogenation step is advantageously followed by at least one, preferably by one step for separation, preferably by distillation, into two different fractions respectively enriched with the compounds comprising less than 5 carbon atoms, for one of them, and enriched with the compounds comprising at least 5 carbon atoms, for the other.

The fraction enriched with the compounds containing less than 5 carbon atoms advantageously comprises at least 80%, preferably at least 90% and in a particularly preferred manner at least 95% by weight relative to the total weight of this fraction, of compounds containing less than 5 carbon atoms.

The fraction enriched with the compounds containing at least 5 carbon atoms advantageously comprises at most 30%, preferably at most 20% and in a particularly preferred manner at most 10% by weight relative to the total weight of this fraction, of compounds containing less than 5 carbon atoms.

In a particularly preferred manner, the fraction enriched with the compounds comprising less than 5 carbon atoms is then conveyed to cracking as raw material while the fraction enriched with the compounds comprising at least 5 carbon atoms is conveyed to cracking as fuel or upgraded in any form.

According to a third subvariant, prior to this step of conveying to cracking, fraction C is advantageously first subjected to at least one, preferably to one separation step consisting in the separation of fraction C, preferably by distillation, into two different fractions respectively enriched with the fractions comprising less than 5 carbon atoms, for one of them, and enriched with the compounds comprising at least 5 carbon atoms, for the other. The resulting fraction, enriched with the compounds comprising less than 5 carbon atoms, is then in a particularly preferred manner subjected to a hydrogenation step before being conveyed to cracking as raw material. As for the fraction enriched with the compounds comprising at least 5 carbon atoms, it is in a particularly preferred manner conveyed to cracking as fuel or upgraded in any form.

The specific characteristics defined for the fraction enriched with the compounds containing less than 5 carbon atoms and that enriched with the compounds containing at least 5 carbon atoms defined above for the second subvariant are applicable for the third subvariant.

In each of the subvariants detailed above, the fraction which is conveyed to cracking as raw material may be conveyed as it is to the cracking oven of the first pyrolysis step or may first of all be mixed with the hydrocarbon source. Preferably, it is mixed with the hydrocarbon source before being conveyed to the cracking oven of the first pyrolysis step. In a particularly preferred manner, the fraction which is conveyed to the cracking oven as raw material is mixed with the hydrocarbon source in an intermediate reservoir before being conveyed to the cracking oven.

In each of the subvariants detailed above, the fraction which is conveyed to cracking as fuel may be conveyed as it is to the cracking oven of the first pyrolysis step or may first of all be mixed with another fuel. Preferably, it is mixed with another fuel before being conveyed to the cracking oven of the first pyrolysis step. In a particularly preferred manner, the fraction which is conveyed to the cracking oven as fuel is mixed with another fuel in an intermediate reservoir before being conveyed to the cracking oven.

The second subvariant explained above is preferred, with a most particular preference for its second embodiment.

The abovementioned hydrogenation step may be performed by means of any known hydrogenation catalyst such as, for example, catalysts based on palladium, platinum, rhodium, ruthenium or iridium deposited on a support such as alumina, silica, silica/alumina, carbon, calcium carbonate or barium sulphate, but also catalysts based on nickel and those based on the cobalt-molybdenum complex. Preferably, the hydrogenation step is performed by means of a catalyst based on palladium or platinum deposited on alumina or carbon, on a catalyst based on nickel or on a catalyst based on the cobalt-molybdenum complex. In a particularly preferred manner, it is performed by means of a catalyst based on nickel.

The temperature at which the hydrogenation step is performed is advantageously at least 5, preferably at least 20, in a particularly preferred manner at least 50° C. It is advantageously at most 150, preferably at most 100° C. As for the pressure, it is advantageously greater than or equal to 1, preferably greater than or equal to 3 bar. It is advantageously less than or equal to 40, preferably less than or equal to 35 bar, in a particularly preferred manner less than or equal to 30 bar, in a most particularly preferred manner less than or equal to 25 bar and most advantageously less than or equal to 20 bar.

Preferably, this hydrogenation step is performed using quantities of hydrogen such that it is complete, that is to say preferably at least 99%. The excess hydrogen not consumed may be separated from the hydrogenated fraction or may be optionally conveyed to the first pyrolysis step with it when this is the case.

According to a second variant of the process according to the invention, fraction C is conveyed to the oven for pyrolysis of DCE, to VC, as fuel.

Another source of energy which may be used to ensure, at least partially, the operation of the oven for pyrolysis of DCE to VC may be advantageously found by burning the products which are not converted during chlorination of ethylene to DCE, in particular hydrogen and methane. These unconverted products may be separated downstream of the chlorination or optionally partially during step a) defined above. Preferably, they are separated downstream of the chlorination. In the latter case, the chlorine-containing products contained in the unconverted products are advantageously removed from the unconverted products before the latter are burnt.

Advantageously, the combustion of 20 to 40%, preferably 30% of these products not converted during chlorination makes it possible to ensure the operation of the pyrolysis oven. The remainder of these products not converted during chlorination can serve as fuel for the cracking oven (in an amount of about 60% for example) or may be upgraded in any form (in an amount of about 10% for example) for example as fuel for an incinerator or a steam boiler.

The heat recovered at the cracking oven, which consists in recovering heat from hot gases (also called sensible heat), may advantageously also be a source of energy, at least partially, to ensure the operation of the oven for pyrolysis of DCE to VC. It may equally well be the sensible heat of the cracked gases and the sensible heat of the gases which served to heat the cracked gas (preheating to the cracking temperature and cracking heat). Preferably, it is the sensible heat of the gases which served to heat the cracked gas.

According to the process of the invention, the separation of the mixture of products containing ethylene and other constituents in step b) leads to the formation of at least one fraction containing ethylene, preferably two fractions containing ethylene, in a particularly preferred manner one fraction containing ethylene which is enriched with the compounds lighter than ethylene, called below fraction A, and a second fraction containing ethylene advantageously enriched with ethylene, called below fraction B and a heavy fraction (fraction C).

According to the process according to the invention, fraction A is advantageously conveyed to the chlorination reactor and fraction B advantageously to the oxychlorination reactor, preferably after expansion with recovery of energy.

According to the process of the invention, the quantities defined below to characterize the fraction B and the fraction A are those before their respective entry into oxychlorination and into chlorination.

Fraction B is advantageously characterized by a hydrogen content of less than or equal to 2%, preferably of less than or equal to 0.5% and in a particularly preferred manner of less than or equal to 0.1% by volume relative to the total volume of fraction B.

Fraction B is characterized by a content of compounds containing at least 3 carbon atoms, advantageously less than or equal to 0.01%, preferably less than or equal to 0.005% and in a particularly preferred manner less than or equal to 0.001% by volume relative to the total volume of fraction B.

Fraction B advantageously contains from 40% to 99.5% by volume of ethylene relative to the total volume of fraction B. Fraction B advantageously contains at least 40%, preferably at least 50% and in a particularly preferred manner at least 60% by volume of ethylene relative to the total volume of fraction B. Fraction B advantageously contains at most 99.5%, preferably at most 99.2% and in a particularly preferred manner at most 99% by volume of ethylene relative to the total volume of fraction B.

In the preferred case where the hydrocarbon source is ethane, fraction B advantageously comprises at least 60%, preferably at least 70% and in a particularly preferred manner at least 75% by volume of ethylene relative to the total volume of fraction B. Fraction B advantageously comprises at most 99.5%, preferably at most 99.2% and in a particularly preferred manner at most 99% by volume of ethylene relative to the total volume of fraction B.

In the preferred case where the hydrocarbon source is a propane/butane mixture, fraction B advantageously comprises at least 40%, preferably at least 50% and in a particularly preferred manner at least 60% by volume of ethylene relative to the total volume of fraction B. Fraction B advantageously comprises at most 99.5%, preferably at most 99.2% and in a particularly preferred manner at most 99% by volume of ethylene relative to the total volume of fraction B.

Fraction B is additionally characterized by an acetylene content which is advantageously less than or equal to 0.01%, preferably less than or equal to 0.005% and in a particularly preferred manner less than or equal to 0.001% by volume relative to the total volume of fraction B.

Fraction A is advantageously enriched with compounds which are lighter than ethylene. These compounds are generally methane, nitrogen, oxygen, hydrogen and carbon monoxide. Advantageously, fraction A contains at least 70%, preferably at least 80% and in a particularly preferred manner at least 85% of compounds lighter than ethylene which are contained in the mixture of products subjected to step b). Advantageously, fraction A contains at most 99.99%, preferably at most 99.97% and in a particularly preferred manner at most 99.95% of compounds lighter than ethylene which are contained in the mixture of products subjected to step b).

In the preferred case where the hydrocarbon source is ethane, fraction A contains at least 90%, preferably at least 95% and in a particularly preferred manner at least 98% of compounds lighter than ethylene which are contained in the mixture of products subjected to step b). Advantageously, fraction A contains at most 99.99%, preferably at most 99.98% and in a particularly preferred manner at most 99.97% of compounds lighter than ethylene which are contained in the mixture of products subjected to step b).

In the preferred case where the hydrocarbon source is a propane/butane mixture, fraction A contains at least 70%, preferably at least 80% and in a particularly preferred manner at least 85% of compounds lighter than ethylene which are contained in the mixture of products subjected to step b). Advantageously, fraction A contains at most 99.99%, preferably at most 99.95% and in a particularly preferred manner at most 99.9% of compounds lighter than ethylene which are contained in the mixture of products subjected to step b).

Fraction A is characterized by a content of compounds containing at least 3 carbon atoms, advantageously less than or equal to 0.01%, preferably less than or equal to 0.005% and in a particularly preferred manner less than or equal to 0.001% by volume relative to the total volume of fraction A.

Fraction A advantageously contains a content by volume of ethylene such that it represents from 10% to 90% of the content by volume of ethylene of fraction B. Fraction A advantageously contains a content by volume of ethylene such that it is less than or equal to 90%, preferably less than or equal to 85% and in a particularly preferred manner less than or equal to 80% of the content by volume of ethylene of fraction B. Fraction A advantageously contains a content by volume of ethylene such that it is at least 10%, preferably at least 15% and in a particularly preferred manner at least 20% of the content by volume of ethylene of fraction B.

In the preferred case where the hydrocarbon source is ethane, fraction A advantageously contains a content by volume of ethylene such that it is less than or equal to 90%, preferably less than or equal to 85% and in a particularly preferred manner less than or equal to 80% of the content by volume of ethylene of fraction B. Fraction A advantageously contains a content by volume of ethylene such that it is at least 15%, preferably at least 20% and in a particularly preferred manner at least 22% of the content by volume of ethylene of fraction B.

In the preferred case where the hydrocarbon source is a propane/butane mixture, fraction A advantageously contains a content by volume of ethylene such that it is less than or equal to 80%, preferably less than or equal to 75% and in a particularly preferred manner less than or equal to 70% of the content by volume of ethylene of fraction B. Fraction A advantageously contains a content by volume of ethylene such that it is at least 10%, preferably at least 15% and in a particularly preferred manner at least 20% of the content by volume of ethylene of fraction B.

Fraction A is additionally characterized by an acetylene content which is advantageously less than or equal to 0.01%, preferably less than or equal to 0.005% and in a particularly preferred manner less than or equal to 0.001% by volume relative to the total volume of fraction A.

According to a first embodiment of the process according to the invention, considering that the process for the manufacture of DCE is advantageously balanced (that is to say that the process of manufacture by chlorination and oxychlorination of ethylene and pyrolysis of the 1,2-dichloroethane (DCE) formed makes it possible to generate the quantity of HCl necessary for the process), the fraction by weight of the ethylene throughput in each of fractions A and B is advantageously between 45 and 55% of the total quantity of ethylene produced (fraction A+fraction B). Preferably, the fraction by weight of the throughput of ethylene in fraction A is of the order of 55% and the fraction by weight of the throughput of ethylene in fraction B is of the order of 45% of the total quantity produced. In a particularly preferred manner, the fraction by weight of the throughput of ethylene in fraction A is of the order of 52.5% and the fraction by weight of the throughput of ethylene in fraction B is of the order of 47.5% of the total quantity produced.

According to a second embodiment of the process according to the invention, considering that the process for the manufacture of DCE is advantageously unbalanced (that is to say for example that an external source of HCl makes it possible to provide part of the supply of HCl for the oxychlorination or that a fraction of the DCE produced is not subjected to pyrolysis), the fraction by weight of the throughput of ethylene in each of fractions A and B is advantageously between 20 and 80% of the total quantity of ethylene produced (fraction A+fraction B). Preferably, the fraction by weight of the throughput of ethylene in fraction A is between 25 and 75% of the total quantity of ethylene produced (fraction A+fraction B).

According to a first variant of the second embodiment of the process according to the invention, considering that the process for the manufacture of DCE is advantageously unbalanced by an external source of HCl, the fraction by mole of the throughput of ethylene in fraction A is advantageously between 45 and 55%, preferably between 50 and 54% and in a particularly preferred manner of the order of 52.5% of the difference between the total molar quantity of ethylene contained in the mixture of products subjected to step b) and the molar quantity of HCl of the external source.

According to a second variant of the second embodiment of the process according to the invention, considering that the process for the manufacture of DCE is advantageously unbalanced by a co-production of DCE (some of the DCE is therefore not subjected to pyrolysis), the fraction by mole of the throughput of ethylene in fraction B is advantageously between 45 and 55%, preferably between 46 and 50% and in a particularly preferred manner of the order of 47.5% of the difference between the total molar quantity of ethylene contained in the mixture of products subjected to step b) and the molar quantity of DCE co-produced.

Any separation process may be used to separate the said mixture of products containing ethylene into fraction A, fraction B and fraction C provided that it advantageously comprises a maximum of four, preferably a maximum of three separation steps in order to obtain both fractions A and B.

According to a first preferred mode of separation, the mixture of products containing ethylene derived from step a) is subjected to a first separation step which makes it possible to extract fraction C therefrom and the resultant mixture is then subjected to a second step for separation into fraction A and fraction B.

According to a second preferred mode of separation, the mixture of products containing ethylene derived from step a) is subjected to a first separation step which makes it possible to extract fraction A therefrom and the resulting mixture is then subjected to a second step for separating into fraction B and fraction C.

The first mode of separation is particularly preferred. Numerous variants can make it possible to carry out this first particularly preferred mode of separation of the mixture of products containing ethylene derived from step a).

A preferred variant of the first mode of separation consists in subjecting the said mixture to a first separation step intended to extract fraction C and then in subjecting the resulting mixture to a second step for separation into fraction A and fraction B which are both distillation steps performed by means of a distillation column equipped with the associated auxiliary equipment such as at least one reboiler and at least one condenser.

According to this preferred variant of the first mode of separation, fraction C advantageously leaves at the bottom of the first distillation column, fraction A at the top of the second distillation column and fraction B at the bottom of the second distillation column.

The distillation column may be chosen from plate distillation columns, packed distillation columns, distillation columns with structured packing and distillation columns combining two or more of the abovementioned internals.

The chlorination reaction is advantageously performed in a liquid phase (preferably mainly DCE) containing a dissolved catalyst such as $FeCl_3$ or another Lewis acid. It is possible to advantageously combine this catalyst with cocatalysts such as alkali metal chlorides. A pair which has given good results is the complex of $FeCl_3$ with LiCl (lithium tetrachloroferrate—as described in patent application NL 6901398).

The quantities of $FeCl_3$ advantageously used are of the order of 1 to 10 g of $FeCl_3$ per kg of liquid stock. The molar ratio of $FeCl_3$ to LiCl is advantageously of the order of 0.5 to 2.

The chlorination process according to the invention is advantageously performed at temperatures of between 30 and 150° C. Good results were obtained regardless of the pressure both at a temperature less than the boiling temperature (under-cooled chlorination) and at the boiling temperature itself (boiling chlorination).

When the chlorination process according to the invention is a under-cooled chlorination, it gave good results by operating at a temperature which is advantageously greater than or equal to 50° C. and preferably greater than or equal to 60° C., but advantageously less than or equal to 80° C. and preferably less than or equal to 70° C.; with a pressure in the gaseous phase advantageously greater than or equal to 1.5 and preferably greater than or equal to 2 absolute bar, but advantageously less than or equal to 20, preferably less than or equal to 10 and in a particularly preferred manner less than or equal to 6 absolute bar.

A boiling chlorination process is particularly preferred which makes it possible, where appropriate, to usefully recover the heat of reaction. In this case, the reaction advantageously takes place at a temperature greater than or equal to 60° C., preferably greater than or equal to 90° C. and in a particularly preferred manner greater than or equal to 95° C. but advantageously less than or equal to 150° C. and preferably less than or equal to 135° C.; with a pressure in the gaseous phase advantageously greater than or equal to 0.2, preferably greater than or equal to 0.5, in a particularly preferred manner greater than or equal to 1.2 and in a most particularly preferred manner greater than or equal to 1.5 absolute bar but advantageously less than or equal to 10 and preferably less than or equal to 6 absolute bar.

The chlorination process may also be a loop under-cooled boiling mixed chlorination process. The expression loop under-cooled boiling mixed chlorination process is understood to mean a process in which cooling of the reaction medium is performed, for example, by means of an exchanger immersed in the reaction medium or by a loop circulating in an exchanger, while producing in a gaseous phase at least the quantity of DCE formed. Advantageously, the reaction temperature and pressure are adjusted for the DCE produced to leave in the gaseous phase and to remove the remainder of the calories from the reaction medium by means of the exchange surface.

In addition, the chlorination process is advantageously performed in a chlorinated organic liquid medium. Preferably, this chlorinated organic liquid medium, also called liquid stock, mainly consists of DCE.

The fraction A containing the ethylene and the chlorine (itself pure or diluted) may be introduced by any known device into the reaction medium together or separately. A separate introduction of the fraction A may be advantageous in order to increase its partial pressure and facilitate its dissolution which often constitutes a limiting step of the process.

The chlorine is added in a sufficient quantity to convert most of the ethylene and without requiring the addition of an excess of unconverted chlorine. The chlorine/ethylene ratio used is preferably between 1.2 and 0.8 and in a particularly preferred manner between 1.05 and 0.95 mol/mol.

The chlorinated products obtained contain mainly DCE and small quantities of by-products such as 1,1,2-trichloroethane or small quantities of chlorination products of ethane or methane. The separation of the DCE obtained from the stream of products derived from the chlorination reactor is carried out according to known modes and makes it possible in general to exploit the heat of the chlorination reaction.

The unconverted products (methane, carbon monoxide, nitrogen, oxygen and hydrogen) are then subjected to an easier separation than what would have been necessary to separate pure ethylene starting with the initial mixture.

The oxychlorination reaction is advantageously performed in the presence of a catalyst comprising active elements including copper deposited on an inert support. The inert support is advantageously chosen from alumina, silica gels, mixed oxides, clays and other supports of natural origin. Alumina constitutes a preferred inert support.

Catalysts comprising active elements which are advantageously at least two in number, one of which is copper, are preferred. Among the active elements other than copper, there may be mentioned alkali metals, alkaline-earth metals, rare-earth metals and metals of the group consisting of ruthenium, rhodium, palladium, osmium, iridium, platinum and gold. The catalysts containing the following active elements are particularly advantageous: copper/magnesium/potassium, copper/magnesium/sodium; copper/magnesium/lithium, copper/magnesium/caesium, copper/magnesium/sodium/lithium, copper/magnesium/potassium/lithium and copper/magnesium/caesium/lithium, copper/magnesium/sodium/potassium, copper/magnesium/sodium/caesium and copper/magnesium/potassium/caesium. The catalysts described in patent applications EP-A 255 156, EP-A 494 474, EP-A-657 212 and EP-A 657 213, incorporated by reference, are most particularly preferred.

The copper content, calculated in metal form, is advantageously between 30 and 90 g/kg, preferably between 40 and 80 g/kg and in a particularly preferred manner between 50 and 70 g/kg of catalyst.

The magnesium content, calculated in metal form, is advantageously between 10 and 30 g/kg, preferably between 12 and 25 g/kg and in a particularly preferred manner between 15 and 20 g/kg of catalyst.

The alkali metal content, calculated in metal form, is advantageously between 0.1 and 30 g/kg, preferably between 0.5 and 20 g/kg and in a particularly preferred manner between 1 and 15 g/kg of catalyst.

The Cu:Mg:alkali metal(s) atomic ratios are advantageously 1:0.1-2:0.05-2, preferably 1:0.2-1.5:0.1-1,5 and in a particularly preferred manner 1:0.5-1:0.15-1.

Catalysts having a specific surface area, measured according to the B.E.T. method with nitrogen, advantageously between 25 $m^2/g$ and 300 $m^2/g$, preferably between 50 and 200 $m^2/g$ and in a particularly preferred manner between 75 and 175 $m^2/g$, are particularly advantageous.

The catalyst may be used in a fixed bed or in a fluidized bed. This second option is preferred. The oxychlorination process is exploited under the range of the conditions usually recommended for this reaction. The temperature is advantageously between 150 and 300° C., preferably between 200 and 275° C. and most preferably from 215 to 255° C. The pressure is advantageously greater than atmospheric pressure. Values of between 2 and 10 absolute bar gave good results. The range between 4 and 7 absolute bar is preferred. This pressure may be usefully modulated in order to obtain an optimum residence time in the reactor and to maintain a constant rate of passage for various speeds of operation. The usual residence times range from 1 to 60 seconds and preferably from 10 to 40 seconds.

The source of oxygen for this oxychlorination may be air, pure oxygen or a mixture thereof, preferably pure oxygen. The latter solution, which allows easy recycling of the unconverted reagents, is preferred.

The reagents may be introduced into the bed by any known device. It is generally advantageous to introduce the oxygen separately from the other reagents for safety reasons. These also require maintaining the gaseous mixture leaving the reactor or recycled thereto outside the limits of inflammability at the pressures and temperatures considered. It is preferable to maintain a so-called rich mixture, that is containing too little oxygen relative to the fuel to ignite. In this regard, the abundant presence (>2%, preferably >5% vol) of hydrogen would constitute a disadvantage given the wide range of inflammability of this compound.

The hydrogen chloride/oxygen ratio used is advantageously between 3 and 6 mol/mol. The ethylene/hydrogen chloride ratio is advantageously between 0.4 and 0.6 mol/mol.

The chlorinated products obtained contain mainly DCE and small quantities of by-products such as 1,1,2-trichloroethane. The separation of the DCE obtained from the stream of products derived from the oxychlorination reactor is carried out according to known modes. The heat of the oxychlorination reaction is generally recovered in vapour form which can be used for the separations or for any other purpose.

The unconverted products such as methane and ethane are then subjected to an easier separation than that which would have been necessary to separate pure ethylene starting from the initial mixture.

The DCE obtained is then separated from the streams of products derived from the chlorination and oxychlorination reactors and conveyed to the pyrolysis oven so as to be advantageously converted to VC therein.

The invention therefore also relates to a process for the manufacture of VC. To this effect, the invention relates to a process for the manufacture of VC, characterized in that the DCE obtained by the process according to the invention is converted to VC in the pyrolysis oven.

The conditions under which the pyrolysis may be carried out are known to persons skilled in the art. This pyrolysis is advantageously obtained by a reaction in the gaseous phase in a tubular oven. The usual pyrolysis temperatures are between 400 and 600° C. with a preference for the range between 480° C. and 540° C. The residence time is advantageously between 1 and 60 s with a preference for the range from 5 to 25 s. The rate of conversion of the DCE is advantageously limited to 45 to 75% in order to limit the formation of by-products and the fouling of the tubes of the oven. The following steps make it possible, using any known device, to collect the purified VC and the hydrogen chloride to be upgraded preferably to the oxychlorination. Following purification, the unconverted DCE is advantageously conveyed to the pyrolysis oven.

In addition, the invention also relates to a process for the manufacture of PVC. To this effect, the invention relates to a process for the manufacture of PVC by polymerization of the VC obtained by the process according to the invention.

The process for the manufacture of PVC may be a mass, solution or aqueous dispersion polymerization process, preferably it is an aqueous dispersion polymerization process.

The expression aqueous dispersion polymerization is understood to mean free radical polymerization in aqueous suspension as well as free radical polymerization in aqueous emulsion and polymerization in aqueous microsuspension.

The expression free radical polymerization in aqueous suspension is understood to mean any free radical polymerization process performed in aqueous medium in the presence of dispersing agents and oil-soluble free radical initiators.

The expression free radical polymerization in aqueous emulsion is understood to mean any free radical polymerization process performed in aqueous medium in the presence of emulsifying agents and water-soluble free radical initiators.

The expression aqueous microsuspension polymerization, also called polymerization in homogenized aqueous dispersion, is understood to mean any free radical polymerization process in which oil-soluble initiators are used and an emulsion of droplets of monomers is prepared by virtue of a powerful mechanical stirring and the presence of emulsifying agents.

The process according to the invention therefore has the advantage, by upgrading the heavy compounds, of substantially improving the economy of the process for the manufacture of DCE.

Another advantage of this process is that, by virtue of the separation of the compounds comprising at least 3 carbon atoms via fraction C, it makes it possible to avoid the problems of inhibition generally encountered during the pyrolysis of DCE when these compounds are carried with ethylene. This inhibition is due to the formation of derivatives such as 1,2-dichloropropane and monochloropropenes. These derivatives are difficult to completely separate from the DCE. Their ease of formation of stable allyl radicals explains their powerful inhibitory effect on the pyrolysis of the DCE which occurs by the free radical route.

The presence of these products containing three and more carbon atoms would moreover constitute an unnecessary consumption of reagents during oxychlorination and during chlorination or would result in costs for destruction. Furthermore, these heavy compounds contribute towards the soiling of the columns and the evaporators.

Another advantage of the process according to the invention is that it makes it possible to have, on the same industrial site, a completely integrated process from the hydrocarbon source to the polymer obtained starting with the monomer manufactured.

BRIEF DESCRIPTION OF DRAWINGS

The process according to the invention will now be illustrated with reference to the drawing accompanying the present description. This drawing consists of the appended FIG. 1, schematically representing one embodiment of the first variant of the process for the manufacture of DCE according to the invention.

The mixture of products 1 containing ethylene and other constituents resulting from the cracking (not shown) of a hydrocarbon source which is ethane introduced into the cracking at a flow rate of 19 984 kg/h is introduced into the main column 2 which is a distillation column equipped with a reboiler at the bottom and a condenser at the top where it is separated into two different fractions, namely fraction 3 at the top of column 2 and fraction 4 at the bottom of column 2.

Figure 1:
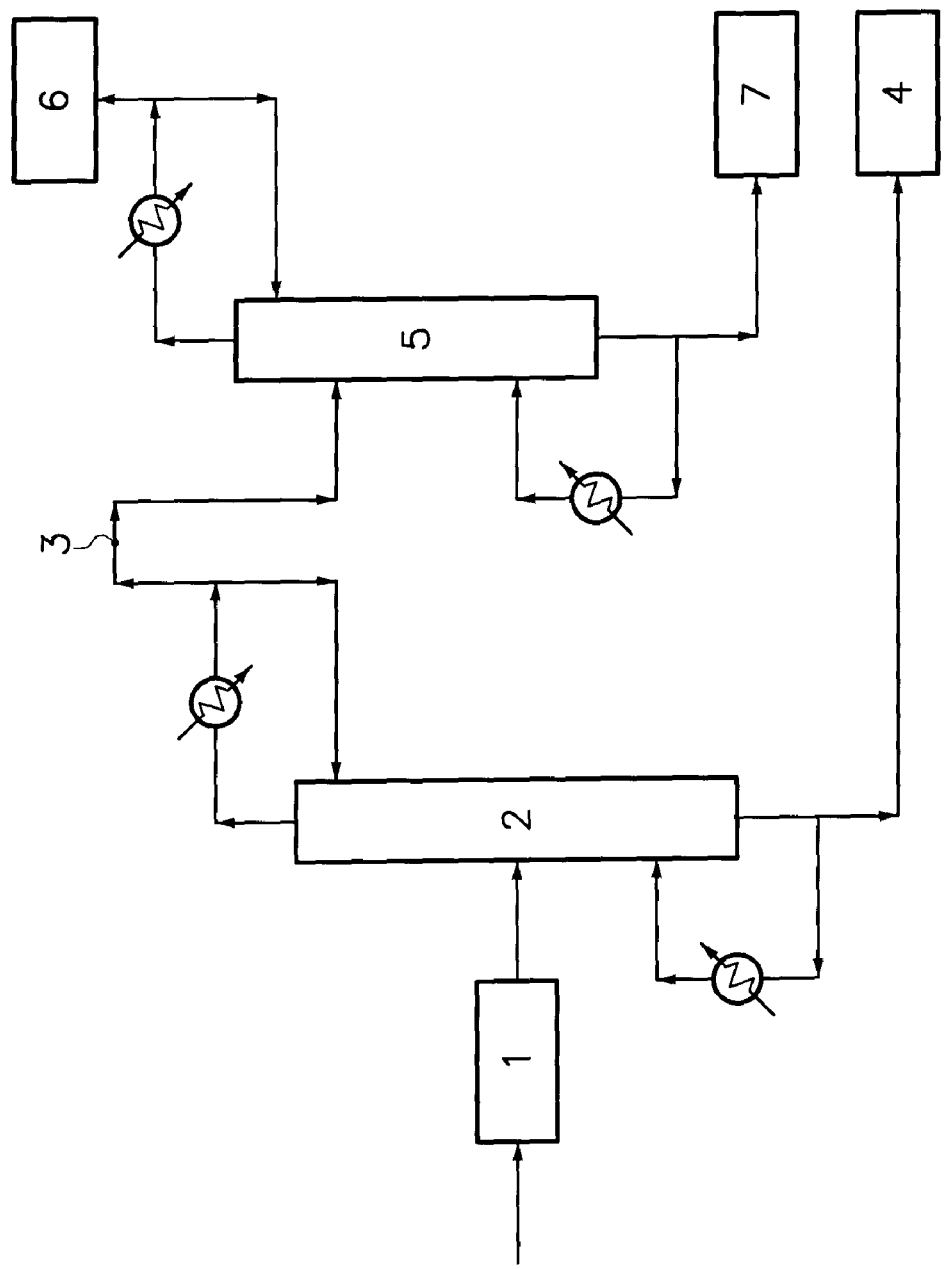

Fraction 3 is then conveyed to a second distillation column 5 equipped with a reboiler at the bottom and a condenser at the top.

Following its passage in column 5, fraction 3 is separated into fraction 6 leaving at the top of column 5 and into fraction 7 leaving at the base of column 5.

Fraction 6, enriched with compounds lighter than ethylene, in particular methane, hydrogen, nitrogen, oxygen and carbon monoxide, is conveyed to the unit for chlorination of ethylene.

Fraction 7, characterized by a very low content of hydrogen, is conveyed to the unit for oxychlorination of ethylene.

Fraction 4, consisting of ethane and the compounds comprising at least 3 carbon atoms, for its part, is either removed (case No. 1), or conveyed as it is to the first cracking step (case No. 2), or subjected to a hydrogenation step followed by a distillation step in order to separate the compounds containing less than 5 carbon atoms from the compounds containing at least 5 carbon atoms and conveying the compounds containing less than 5 carbon atoms to the first cracking step (case No. 3).

The yield of ethylene contained in fractions 6 and 7 relative to the ethane used for the 3 cases described above is 56, 83 and 89%, respectively.

These figures advantageously illustrate the economic benefit which the upgrading of fraction 4 (heavy fraction C) represents.

The invention claimed is:

1. A process for the manufacture of 1,2-dichloroethane from a hydrocarbon source comprising:
   a) subjecting said hydrocarbon source to cracking to produce a product mixture comprising ethylene and other constituents;
   b) separating said product mixture into at least one ethylene fraction having a purity of less than 99.8% and into a heavy fraction C comprising ethane and compounds comprising at least 3 carbon atoms;
   c) conveying said at least one ethylene fraction to a chlorination reactor and/or an oxychlorination reactor to convert most of the ethylene present within said at least one ethylene fraction into 1,2-dichloroethane;
   d) separating said 1,2-dichloroethane from one or more streams of products derived from said chlorination reactor and/or said oxychlorination reactor and conveying said 1,2-dichloroethane to a pyrolysis oven; and
   e) conveying said heavy fraction C to said pyrolysis oven in d) as fuel.

2. The process for the manufacture of 1,2-dichloroethane according to claim 1, wherein said hydrocarbon source is selected from the group consisting of naphtha, gas oil, natural gas liquid, ethane, propane, butane, isobutane and mixtures thereof.

3. The process for the manufacture of 1,2-dichloroethane according to claim 1, wherein said hydrocarbon source is selected from the group consisting of ethane, propane, butane and propane/butane mixtures.

4. The process according to claim 1, wherein said product mixture in a) comprises ethylene, hydrogen, methane, compounds comprising from 2 to 7 carbon atoms, carbon monoxide, nitrogen and oxygen.

5. A process for the manufacture of 1,2-dichloroethane from a hydrocarbon source comprising:
 a) subjecting said hydrocarbon source to cracking to produce a product mixture comprising ethylene and other constituents;
 b) separating said product mixture into at least one ethylene fraction and into a heavy fraction C;
 c) conveying said at least one ethylene fraction to a chlorination reactor and/or an oxychlorination reactor to convert most of the ethylene present within said at least one ethylene fraction into 1,2-dichloroethane;
 d) separating said 1,2-dichloroethane from one or more streams of products derived from said chlorination reactor and/or said oxychlorination reactor and conveying said 1,2-dichloroethane to a pyrolysis oven; and
 e) conveying said heavy fraction C to said cracking in a) or to said pyrolysis oven in d) as fuel,
 wherein said separating in b) of said product mixture leads to the formation of an ethylene fraction A enriched with compounds lighter than ethylene, an ethylene fraction B enriched with ethylene and said heavy fraction C.

6. The process according to claim 5, wherein said ethylene fraction B comprises from 40% to 99.5% by volume of ethylene relative to the total volume of said ethylene fraction B.

7. The process according to claim 5, wherein said ethylene fraction A comprises from 10% to 90% by volume of ethylene relative to the volume of ethylene present within said ethylene fraction B.

8. The process according to claim 5, wherein said ethylene fraction A is conveyed to said chlorination reactor and said ethylene fraction B is conveyed to said oxychlorination reactor.

9. The process according to claim 1, further comprising pyrolysis of said 1,2-dichloroethane in a pyrolysis oven to convert said 1,2-dichloroethane to vinyl chloride.

10. The process according to claim 9, further comprising polymerizing said vinyl chloride to form polyvinyl chloride.

11. The process for the manufacture of 1,2-dichloroethane according to claim 5, wherein said hydrocarbon source is selected from the group consisting of ethane, propane, butane and propane/butane mixtures.

12. The process for the manufacture of 1,2-dichloroethane according to claim 5, wherein said heavy fraction C is conveyed to said cracking in a).

13. The process for the manufacture of 1,2-dichloroethane according to claim 12, wherein said heavy fraction C is conveyed to a first part of said cracking in a) which is a pyrolysis.

14. The process for the manufacture of 1,2-dichloroethane according to claim 5, wherein said heavy fraction C is conveyed to said pyrolysis oven in d) as fuel.

15. The process according to claim 5, further comprising pyrolysis of said 1,2-dichloroethane in a pyrolysis oven to convert said 1,2-dichloroethane to vinyl chloride.

16. The process according to claim 15, further comprising polymerizing said vinyl chloride to form polyvinyl chloride.

17. The process according to claim 5, wherein said product mixture in a) comprises ethylene, hydrogen, methane, compounds comprising from 2 to 7 carbon atoms, carbon monoxide, nitrogen and oxygen.

18. The process according to claim 1, wherein said separating in b) of said product mixture leads to the formation of an ethylene fraction A enriched with compounds lighter than ethylene, an ethylene fraction B enriched with ethylene and said heavy fraction C.

19. The process according to claim 18, wherein said ethylene fraction A comprises from 10% to 90% by volume of ethylene relative to the volume of ethylene present within said ethylene fraction B, wherein said ethylene fraction B comprises from 40% to 99.5% by volume of ethylene relative to the total volume of said ethylene fraction B, and wherein said ethylene fraction A is conveyed to said chlorination reactor and said ethylene fraction B is conveyed to said oxychlorination reactor.

20. The process according to claim 5, wherein heavy fraction C comprises ethane and compounds comprising at least 3 carbon atoms.

* * * * *